(12) United States Patent
Yokota

(10) Patent No.: US 9,451,872 B2
(45) Date of Patent: Sep. 27, 2016

(54) ENDOSCOPE AND IMAGE ACQUISITION METHOD

(71) Applicant: OLYMPUS CORPORATION, Shibuya-ku, Tokyo (JP)

(72) Inventor: Masayoshi Yokota, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 226 days.

(21) Appl. No.: 14/079,357

(22) Filed: Nov. 13, 2013

(65) Prior Publication Data

US 2014/0066784 A1 Mar. 6, 2014

Related U.S. Application Data

(63) Continuation of application No. PCT/JP2012/063271, filed on May 24, 2012.

(30) Foreign Application Priority Data

May 24, 2011 (JP) .................. 2011-116091

(51) Int. Cl.
*A61B 1/06* (2006.01)
*A61B 1/00* (2006.01)
(Continued)

(52) U.S. Cl.
CPC ........... *A61B 1/00006* (2013.01); *A61B 1/045* (2013.01); *A61B 1/05* (2013.01);
(Continued)

(58) Field of Classification Search
CPC .... A61B 1/0638; A61B 1/0009; A61B 1/06; A61B 1/0646; A61B 1/0661; A61B 1/05; A61B 5/1079; A61B 5/0084; G06T 7/0024
USPC ............... 600/160, 172, 175, 178, 180, 181; 348/45, 65
See application file for complete search history.

(56) References Cited

U.S. PATENT DOCUMENTS 5,784,098 A 7/1998 Shoji et al.
2005/0061062 A1 3/2005 Kaneko et al.
(Continued)

FOREIGN PATENT DOCUMENTS

JP 03-128043 A 5/1991
JP 05-211988 A 8/1993
(Continued)

OTHER PUBLICATIONS

Extended European Search Report (EESR) dated Mar. 13, 2014 (in English) issued in counterpart European Application No. 12788847.7.

(Continued)

*Primary Examiner* — Anhtuan T Nguyen
*Assistant Examiner* — Timothy J Neal
(74) *Attorney, Agent, or Firm* — Holtz, Holtz & Volek PC

(57) ABSTRACT

An endoscope configured to measure a specimen using a pattern projection image of the specimen on which a light and shade pattern of light is projected, the endoscope may include: an insertion unit; an image capturing unit installed at a tip section of the insertion unit and configured to acquire an image of the specimen; an illumination unit having a first light source configured to emit illumination light to illuminate an observation field of vision of the image capturing unit; a pattern projection unit having a second light source configured to emit projection light to project the light and shade pattern on the specimen; and a control unit configured to control an operation of acquiring the image by the image capturing unit, an operation of emitting the illumination light from the illumination unit, and an operation of emitting the projection light from the pattern projection unit.

10 Claims, 4 Drawing Sheets

(51) Int. Cl.
  *A61B 1/05*   (2006.01)
  *A61B 5/107*  (2006.01)
  *A61B 5/00*   (2006.01)
  *A61B 1/045*  (2006.01)
  *A61B 6/00*   (2006.01)

(52) U.S. Cl.
  CPC .............. *A61B 1/06* (2013.01); *A61B 5/0084* (2013.01); *A61B 5/1077* (2013.01); *A61B 5/1079* (2013.01); *A61B 1/00009* (2013.01); *A61B 1/00039* (2013.01); *A61B 1/0684* (2013.01)

(56) References Cited

U.S. PATENT DOCUMENTS

| | | |
|---|---|---|
| 2005/0090749 A1 | 4/2005 | Rubbert |
| 2009/0225321 A1 | 9/2009 | Bendall et al. |
| 2009/0244260 A1 | 10/2009 | Takahashi et al. |
| 2010/0268069 A1 | 10/2010 | Liang |
| 2010/0303341 A1 | 12/2010 | Hausler |
| 2011/0267444 A1* | 11/2011 | Yamaguchi ........ A61B 1/00009 348/65 |
| 2011/0287387 A1 | 11/2011 | Chen et al. |

FOREIGN PATENT DOCUMENTS

| | | |
|---|---|---|
| JP | 09-061132 A | 3/1997 |
| JP | 2005-091265 A | 4/2005 |
| JP | 2009-061014 A | 3/2009 |
| JP | 2009-240621 A | 10/2009 |

OTHER PUBLICATIONS

International Search Report (ISR) dated Jul. 10, 2012 (and English translation thereof) issued in International Application No. PCT/JP2012/063271.

* cited by examiner

ENDOSCOPE AND IMAGE ACQUISITION METHOD

CROSS REFERENCE TO RELATED APPLICATIONS

This application is a continuation application based on a PCT Patent Application No. PCT/JP2012/063271, filed May 24, 2012, whose priority is claimed on Japanese Patent Application No. 2011-116091, filed May 24, 2011, the entire content of which are hereby incorporated by reference.

BACKGROUND OF THE INVENTION

1. Field of the Invention

The present invention relates to an endoscope and an image acquisition method, and more specifically, to an endoscope configured to project a pattern such as stripes or the like on a specimen and measure a 3-dimensional shape of a specimen surface, and a method of acquiring a plurality of images using the endoscope.

2. Description of the Related Art

In the related art, in order to inspect a specimen, an endoscope including a long insertion unit and having an observation unit such as an optical system, an image pickup device, or the like, installed at a tip of the insertion unit is used. In such endoscopes, an endoscope configured to acquire a plurality of stripe images formed by projecting a stripe pattern on a specimen while deviating a phase of the stripe pattern and calculate a 3-dimensional shape of the specimen by a known phase shift method using the plurality of stripe images is already known. For example, US Patent Application, Publication No. 2009/0225321 discloses an endoscope having two projection windows configured to project stripes and installed at a tip surface of an insertion unit.

SUMMARY

The present invention provides an endoscope and an image acquisition method that are capable of suppressing a positional deviation between a plurality of acquired images.

According to a first aspect of the present invention, an endoscope is configured to measure a specimen using a pattern projection image of the specimen on which a light and shade pattern of light is projected, and includes an insertion unit, an image capturing unit, an illumination unit, a pattern projection unit and a control unit. The image capturing unit is installed at a tip section of the insertion unit and configured to acquire an image of the specimen. The illumination unit has a first light source configured to emit illumination light to illuminate an observation field of vision of the image capturing unit. The pattern projection unit has a second light source configured to emit projection light to project the light and shade pattern on the specimen. The control unit is configured to control an operation of acquiring the image by the image capturing unit, an operation of emitting the illumination light from the illumination unit, and an operation of emitting the projection light from the pattern projection unit, and based on a time from starting of emission of the illumination light from the first light source until light quantity of the illumination light arrives at a light quantity needed to acquire the image, and a time from starting emission of the projection light from the second light source until light quantity of the projection light arrives at a light quantity needed to acquire the image, acquires a first image and a second image of the specimen by the image capturing unit. The control unit operates first one of the illumination unit and the pattern projection unit, which has a longer time until the light quantity arrives at the light quantity needed to acquire the image, so that the first image of the specimen is acquired by the image capturing unit. The control unit operates the other of the illumination unit and the pattern projection unit, which has a short time until the light quantity arrives at the light quantity needed to acquire the image, after acquisition of the first image, so that the second image of the specimen is acquired by the image capturing unit.

According to a second aspect of the present invention, in the control unit, based on a time from starting of supply stoppage of the illumination light until the light quantity of the illumination light is reduced to a light quantity that does not exert an influence on acquisition of the image, and a time from starting of supply stoppage of the projection light until the light quantity of the projection light is reduced to a light quantity that does not exert an influence on acquisition of the image, the first image and the second image of the specimen are acquired by the image capturing unit. The control unit operates first one of the illumination unit and the pattern projection unit, which as a short time until the light quantity is reduced to a light quantity that does not exert an influence on acquisition of the image, so that the first image of the specimen is acquired by the image capturing unit. The control unit operates the other of the illumination unit and the pattern projection unit, which has a long time until the light quantity is reduced to a light quantity that does not exert an influence on acquisition of the image, after acquisition of the first image, so that the second image of the specimen is acquired by the image capturing unit.

According to a third aspect of the present invention, in the control unit, when a total time of a time from starting of supply stoppage of the illumination light until the light quantity of the illumination light is reduced to a light quantity that does not exert an influence on acquisition of the image, and a time from starting of emission of the illumination light from the second light source until the light quantity of the illumination light arrives at a light quantity needed to acquire the image is smaller than a total time of a time from starting of supply stoppage of the projection light until the light quantity of the projection light is reduced to a light quantity that does not exert an influence on acquisition of the image, and a time from starting of emission of the illumination light from the first light source until the light quantity of the illumination light arrives at a light quantity needed to acquire the image, the illumination unit is operated first so that the first image of the specimen is acquired by the image capturing unit, and then the pattern projection unit is operated so that the second image of the specimen is acquired by the image capturing unit. In addition, in the control unit, when a total time of a time from starting of supply stoppage of the illumination light until the light quantity of the illumination light is reduced to a light quantity that does not exert an influence on acquisition of the image, and a time from starting of emission of the illumination light from the second light source until the light quantity of the illumination light arrives at a light quantity needed to acquire the image is larger than a total time of a time from starting supply stoppage of the projection light until the light quantity of the projection light is reduced to a light quantity that does not exert influence on acquisition of the image, and a time from emission of the illumination light from the first light source until the light quantity of the illumination light arrives at a light quantity needed to acquire the image, the pattern projection unit is operated first so that the first image of the specimen is acquired by the image capturing unit, and then the illumination unit is operated so that the second image of the specimen is acquired by the image capturing unit.

Preferably, the supply stoppage of the illumination light may include stoppage of the first light source that emits the illumination light.

Preferably, the supply stoppage of the illumination light may include blocking of the illumination light.

Preferably, the supply stoppage of the projection light may include stoppage of the second light source that emits the projection light.

Preferably, the supply stoppage of the projection light may include blocking of the projection light.

Preferably, a shutter configured to switch an emission state of light may be installed at at least one of the first light source and the second light source.

According to a fourth aspect of the present invention, the control unit may include a blur detection unit configured to select at least two images from the image of the specimen acquired in a state in which the illumination light is radiated and the image of the specimen acquired in a state in which the projection light is radiated, and detect a blur of the insertion unit and the specimen based on a deviation amount of the two images.

According to a fifth aspect of the present invention, an image acquisition method of radiating illumination light to a specimen to acquire an image of the specimen and projecting a stripe pattern on the specimen to acquire an image of the specimen using projection light, using an endoscope, includes: based on a time from starting of emission of the illumination light until a light quantity of the illumination light arrives at a light quantity needed to acquire the image, and a time from starting of emission of the projection light until a light quantity of the projection light arrives at a light quantity needed to acquire the image, acquiring a first image of the specimen using one of the illumination light and the projection light having a long time until the light quantity is stabilized; and acquiring a second image of the specimen using the other of the illumination light and the projection light having a short time until the light quantity arrives at a light quantity needed to acquire the image, after the first image is acquired.

DESCRIPTION OF THE PREFERRED EMBODIMENTS

Hereinafter, an endoscope and an image acquisition method of an embodiment of the present invention will be described.

Figure 1:
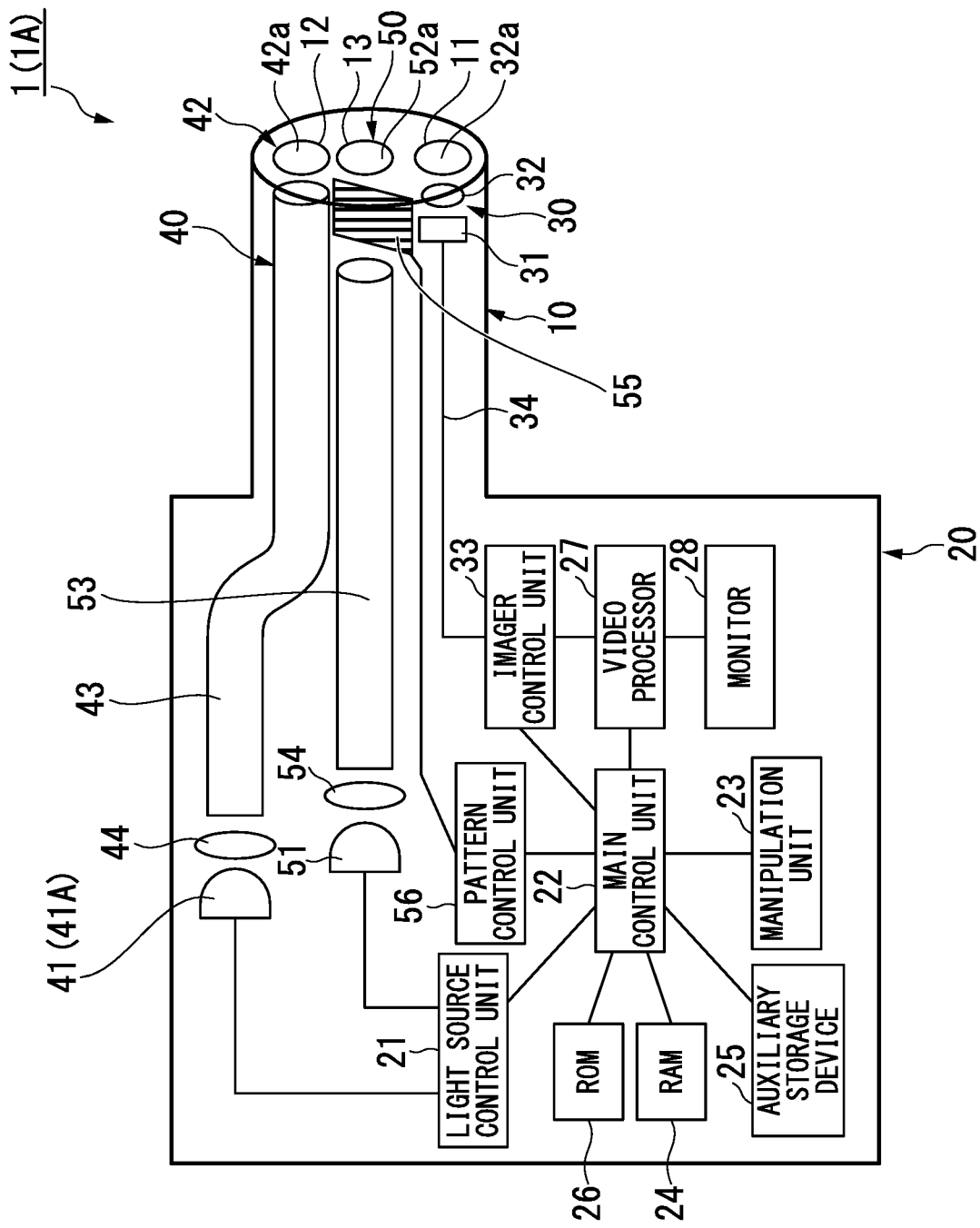
FIG. 1 is a block diagram showing a constitution of an endoscope of an embodiment of the present invention.
Figure 2:
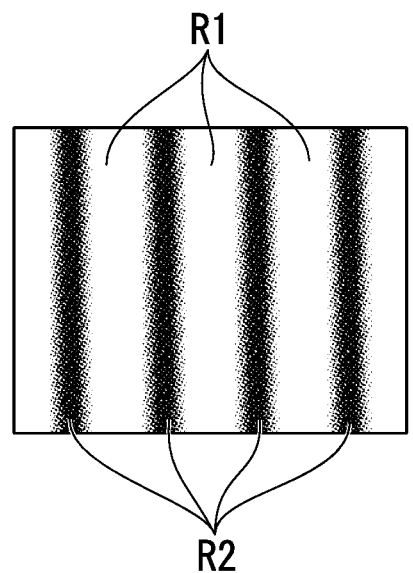
FIG. 2 is a schematic view showing a light and shade pattern projected by the endoscope of the embodiment of the present invention.

First, a constitution of an endoscope 1 of the embodiment will be described. FIG. 1 is a block diagram showing a constitution of the endoscope 1. FIG. 2 is a schematic view showing a light and shade pattern projected by the endoscope 1.

The endoscope 1 is used in internal observation of the specimen, observation of the specimen disposed at a position that a conventional observation apparatus cannot easily access, or the like. The endoscope 1 includes a long insertion unit 10, and a main body section 20 to which a base end of the insertion unit 10 is connected.

As shown in FIG. 1, the insertion unit 10 is formed in a tubular shape. The insertion unit 10 is inserted into the specimen or an access path to the specimen. An image capturing unit 30, an illumination unit 40 and a pattern projection unit 50 are installed at the insertion unit 10. The image capturing unit 30 acquires an image of the specimen. The illumination unit 40 illuminates an observation field of vision in front of the insertion unit 10. The pattern projection unit 50 projects a light and shade pattern on the specimen.

In addition, an opening 11, an illumination window 12 and a projection window 13 are installed at a tip surface 10a of the insertion unit 10. External light enters an object optical system 32 of the image capturing unit 30 through the opening 11. The illumination window 12 irradiates the illumination light from the illumination unit 40 to a forward side of the insertion unit. The projection window 13 irradiates the light and shade pattern from the pattern projection unit 50 to the forward side of the insertion unit. In the embodiment, the pattern projection unit 50 projects the stripe pattern, which is a light and shade pattern, on the specimen.

The image capturing unit 30 includes an imager 31, the object optical system 32 and a control unit 33. The imager 31 is disposed in the vicinity of the tip of the insertion unit 10. The object optical system 32 is disposed in front of the imager 31. The control unit 33 is connected to the imager 31.

Various known constitutions including various image sensors such as CCD, CMOS, or the like, may be used as the imager 31.

The object optical system 32 is disposed in the opening 11 of the insertion unit 10. The object optical system 32 has a predetermined angle of view. The object optical system 32 allows incidence of the reflective light in an observation field of vision defined by the angle of view into the imager 31, and forms an image of the specimen. In addition, the object optical system 32 has a cover member 32a having optical transparency. The cover member 32a seals the opening 11.

The imager control unit 33 is installed in the main body section 20. In addition, the imager control unit 33 is connected to the imager 31 by a wiring 34 extending in the insertion unit 10. The imager control unit 33 performs various controls such as driving of the imager 31, setting of acquiring the video signal, and so on.

The illumination unit 40 includes a first light source 41, an illumination optical system 42, a first fiber bundle 43 and a first incidence optical system 44. The first fiber bundle 43 guides light of the first light source 41 to the illumination optical system 42. The first incidence optical system 44 is disposed between the first light source 41 and the first fiber bundle 43.

The first light source 41 is a light source configured to emit white light. The first light source 41 is disposed in the main body section 20. A known light source such as a halogen lamp, a mercury lamp, or the like, may be appropriately selected and employed as the first light source 41. In the embodiment, the halogen lamp is employed as the first light source 41. The light emitted from the first light source 41 is illumination light configured to illuminate the specimen.

The illumination optical system 42 is attached to the tip or the vicinity of the tip of the insertion unit 10. The illumination optical system 42 has a cover member 42a having optical transparency, and a lens group (not shown). The cover member 42a is installed in the illumination window 12 of the insertion unit 10. The illumination optical system 42 outputs the light radiated from the first light source 41 through the illumination window 12 to be spread to a field of vision range appropriate for the angle of view of the object optical system 32, and illuminates all over the observation field of vision.

The first fiber bundle 43 extends from the vicinity of the illumination optical system 42 to the vicinity of the first light source 41 in the main body section 20 through the insertion unit 10. The kind of the first fiber bundle 43 is not particularly limited but a general light guide may be used.

The first incidence optical system 44 converges the light emitted from the first light source 41 to substantially the same diameter as the first fiber bundle 43 and efficiently guides the light into the first fiber bundle 43.

The pattern projection unit 50 includes a second light source 51, a projection optical system 52, a second fiber bundle 53, a second incidence optical system 54 and a pattern generating unit 55. The second fiber bundle 53 guides the light of the second light source 51 into the projection optical system 52. The second incidence optical system 54 is disposed between the second light source 51 and the second fiber bundle 53. The pattern generating unit 55 is disposed on an optical path of the light emitted from the second light source 51.

The second light source 51 is a light source configured to emit light different from the first light source 41. The second light source 51 is disposed in the main body section 20. An LED light source, a laser light source, or the like, may be employed as the second light source 51. In the embodiment, the LED light source is employed as the second light source 51. The light emitted from the second light source 51 is projection light configured to project the stripe pattern.

The projection optical system 52 is attached to the tip or the vicinity of the tip of the insertion unit 10. The projection optical system 52 has a cover member 52a having optical transparency. The cover member 52a is disposed in the projection window 13 of the insertion unit 10. In addition, the cover member 52a installed at the projection window 13 may be configured in a lens shape. The projection optical system 52 spreads the light radiated from the second light source 51 to a field of vision range appropriate for the angle of view of the object optical system 32 and projects the light from the one projection window 13 into the field of vision.

The second fiber bundle 53 extends from the vicinity of the projection optical system 52 to the vicinity of the second light source 51 in the main body section 20 through the insertion unit 10. Like the first fiber bundle 43, a general light guide may be used as the second fiber bundle 53.

The second incidence optical system 54 converges the light emitted from the second light source 51 to substantially the same diameter as the second fiber bundle 53 and efficiently guides the light into the second fiber bundle 53.

The pattern generating unit 55 is configured to be formed in a stripe pattern. For example, a slit plate having a plurality of slits, or a transparent plate formed of glass, resin, or the like, on which a stripe pattern is drawn, may be used.

Moreover, the pattern generating unit 55 may use a liquid crystalline shutter module configured to switch penetration and non-penetration of the light to each element, a microelectromechanical system (MEMS) mirror module including a minute reflecting mirror installed at each element, or the like. In this case, as each element is individually controlled, since a stripe pattern having an appropriate phase can be formed without movement of the entire pattern generating unit 55, a constitution of the pattern projection unit 50 can be simplified. Switching of the stripe pattern is performed by a pattern control unit 56 connected to the pattern generating unit 55.

The above-mentioned imager control unit 33, a light source control unit 21 and a main control unit 22 are installed in the main body section 20. The light source control unit 21 controls an operation of emitting illumination light from the illumination unit 40 and an operation of emitting projection light from the pattern projection unit 50.

A video processor 27 and the main control unit 22 are connected to the imager control unit 33. The video processor 27 processes the video signal acquired by the imager 31. The main control unit 22 controls an operation of the imager control unit 33. The video processor 27 and the main control unit 22 are installed in the main body section 20.

A monitor 28 is connected to the video processor 27. The monitor 28 displays the video signal processed by the video processor 27 as an image.

The light source control unit 21 is connected to the first light source 41, the second light source 51 and the main control unit 21. The light source control unit 21 controls ON/OFF of the first light source 41 and the second light source 51 based on the control by the main control unit 22.

The main control unit 22 is further connected to a manipulation unit 23, a RAM 24, a ROM 26, an auxiliary storage device 25, and the pattern control unit 56.

The manipulation unit 23 has a switch or the like configured to allow a user to input various items into the endoscope 1.

In addition, a touch panel installed to overlap a display screen of the monitor 28 may be employed as the manipulation unit 23.

The RAM 24 functions as a work area used upon the image capturing of the specimen, measurement of the 3-dimensional shape, or the like, using the endoscope 1.

For example, firmware or the like is recorded on the ROM 26. The ROM 26 is configured to read the firmware or the like upon starting of the endoscope 1.

The auxiliary storage device 25 may employ, for example, a storage device, a magnetic storage device, or the like, having a nonvolatile memory, which is rewritable.

Next, a constitution of the main control unit 22 will be described in detail.

A time wa (see FIG. 4) from starting of emission of the illumination light from the first light source 41 to stabilization of light quantity of the illumination light and a time wb (see FIG. 4) from starting of emission of the projection light from the second light source 51 to stabilization of light quantity of the projection light are previously stored in the main control unit 22.

These times can be determined according to the kind of light source or based on the measured value.

In the embodiment, as the first light source 41 is a halogen lamp and the second light source 51 is an LED light source, a relation is set such that the time wa is longer than the time wb.

The main control unit 22 first operates one of the illumination unit 40 and the pattern projection unit 50, which has a longer time until the light quantity is stabilized, based on the above-mentioned time wa and time wb. The other of the illumination unit 40 and the pattern projection unit 50, which has a shorter time until the light quantity is stabilized, is operated after that.

The main control unit 22 acquires an image of the specimen in a state in which the illumination light is radiated (hereinafter referred to as a "bright field image") and an image of the specimen in a state in which the stripe pattern is projected by the projection light (hereinafter referred to as a "pattern projection image") at the image capturing unit 30 by controlling the imager control unit 33. In the embodiment, a first image is an image in which the bright field image is acquired first. In addition, a second image is an image in which the pattern projection image is acquired after that.

Further, the main control unit 22 includes a blur detection unit configured to select at least two images from the bright field image and the pattern projection image and detect a blur between the insertion unit 10 and the specimen based on a deviation amount of the selected two images.

A threshold value of the deviation amount allowed in the two images is previously stored in the blur detection unit.

The blur detection unit detects the deviation amount in the two images by a known unit. When the deviation amount in the two images exceeds the threshold value, the blur detection unit determines that there is a relative movement (hereinafter referred to as a "blur") between the insertion unit 10 and the specimen.

Further, the main control unit 22 is configured such that a measuring program of measuring a 3-dimensional shape of the specimen can be operated using the pattern projection image.

Next, an image acquisition method of the embodiment will be described with an operation in use of the endoscope 1.

Figure 3:
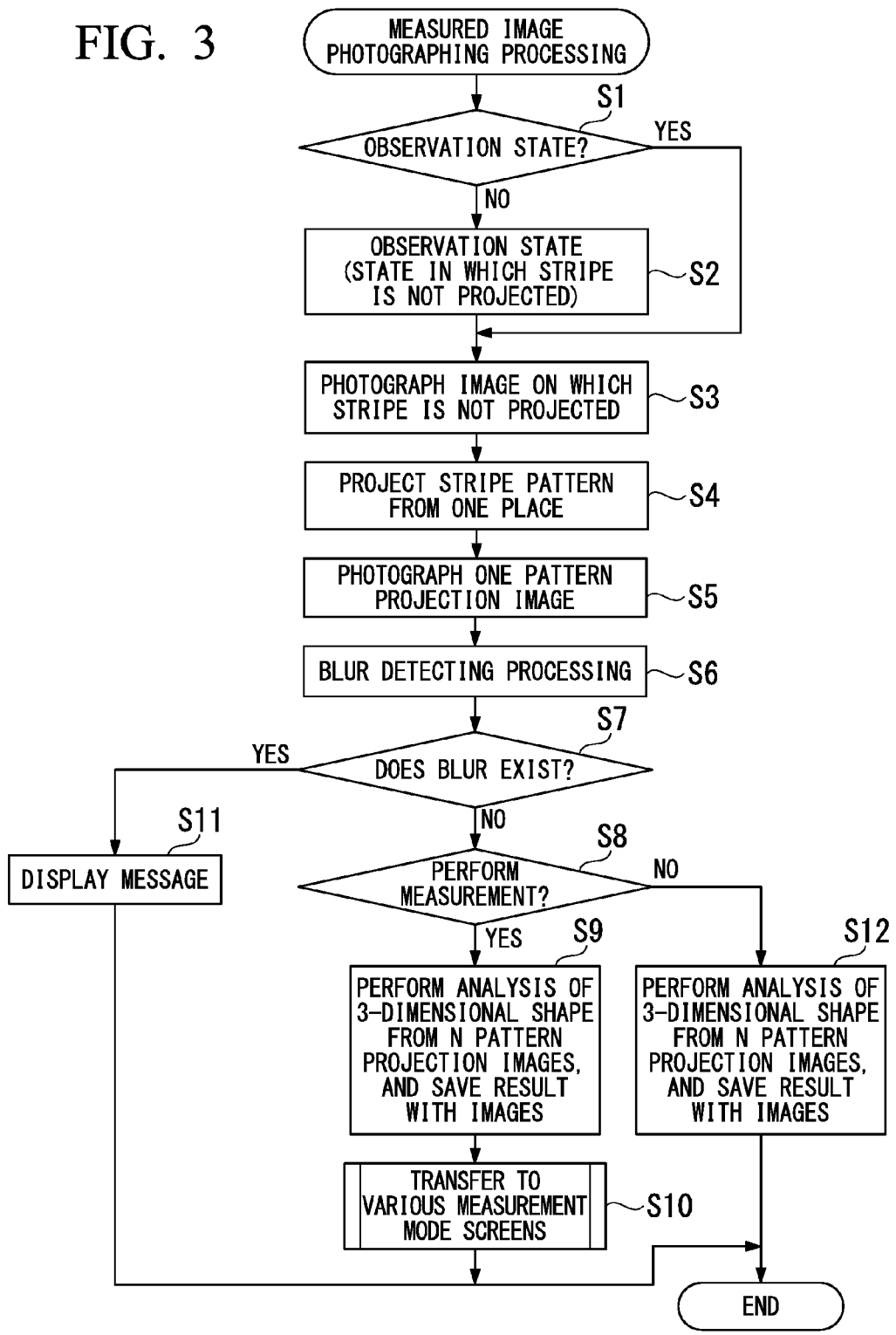
FIG. 3 is a flowchart for describing an operation in use of the endoscope of the embodiment of the present invention.
Figure 4:
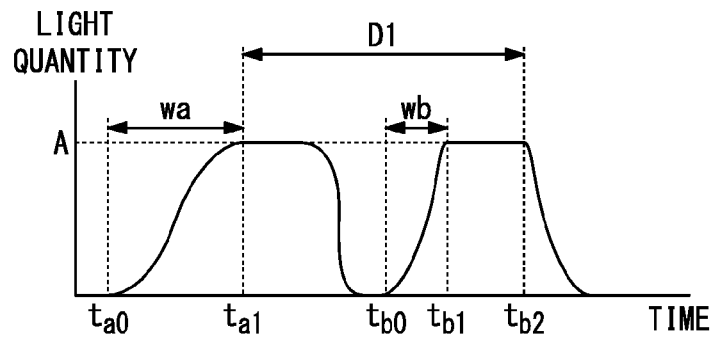
FIG. 4 is a graph showing a relation between a light quantity and time in use of the endoscope of the embodiment of the present invention.

FIG. 3 is a flowchart for describing an operation in use of the endoscope 1. FIG. 4 is a graph showing a relation between a light quantity and a time in use of the endoscope 1.

The image acquisition method of the embodiment is a method including irradiating the specimen with illumination light and acquiring an image of a specimen using the endoscope, and projecting a stripe pattern on the specimen using projection light and acquiring the image of the specimen. In addition, the endoscope 1 of the embodiment can measure the 3-dimensional shape of the specimen using the obtained image.

In use of the endoscope 1, first, a user inserts the insertion unit 10 into the specimen or an access path to the specimen, for example, a conduit line, or the like, and moves the tip of the insertion unit 10 forward to a predetermined observation area. The user performs inspection or the like of the specimen by switching an observation mode of observing a predetermined area of the specimen and a measuring mode of measuring a 3-dimensional shape of the observation area according to necessity.

In the observation mode, the light source control unit 21 receives an instruction of the main control unit 22, turns the first light source 41 on, and turns the second light source 51 off. As a result, the stripe pattern is not projected from the pattern projection unit 50, and white light is radiated from the illumination unit 40 to the observation field of vision so that the observation field of vision is illuminated (hereinafter, this illumination state is referred to as an "observation state"). An image of the illuminated specimen is imaged on the imager 31 through the object optical system 32. A video signal transmitted from the imager 31 is processed in the video processor 27 and displayed on the monitor 28. The user can observe the specimen by the image of the specimen displayed on the monitor 28, and store the image according to necessity.

When the observation mode is switched to the measuring mode, the user inputs an instruction of switching the mode. When the instruction of switching the observation mode to the measuring mode is input by the user, measuring image photographing (see FIG. 3) is started in the main control unit 22.

In the measuring image photographing, first, it is determined whether the endoscope 1 is in the observation state or not (step S1 shown in FIG. 3).

In step S1, when it is determined that the endoscope 1 is in the observation state, step S3 is performed. When the endoscope 1 is in a state other than the observation state (for example, a measurement state, which is to be described below) in step S1, step S2 is performed.

Here, step S1 is terminated.

Step S2 is a step of switching the endoscope 1 to the observation state.

In step S2, the first light source 41 is turned on and the second light source 51 is turned off. Accordingly, the stripe pattern from the pattern projection unit 50 is not projected and the white light is radiated from the illumination unit 40 to the observation field of vision so that the observation field of vision is illuminated.

As shown in FIG. 4, when the first light source 41 is turned on at a time $t_{a0}$ in step S2, the light quantity of the first light source 41 is increased, and the light quantity of the first light source 41 at the time $t_{a1}$ is stabilized. In the embodiment, after the time $t_{a1}$ in which the light quantity of the first light source 41 is stabilized, the bright field image can be acquired.

Here, step S2 is terminated, and step S3 is performed.

Step S3 is a step of photographing the image of the specimen illuminated by the illumination light from the illumination unit 40. Here, the stripe pattern is not projected.

In step S3, an image (a bright field image) is acquired by the imager 31 of the image capturing unit 30 in a state in which the specimen is illuminated by the illumination light from the illumination unit 40.

The bright field image photographed in step S3 is temporarily stored in the RAM 24.

Here, step S3 is terminated, and step S4 is performed.

Step S4 is a step of projecting the stripe pattern on the specimen.

In step S4, based on the instruction of the main control unit 22, the first light source 41 is turned off and the second light source 51 is turned on. As shown in FIG. 4, when the second light source 51 is turned on at a time $t_{b0}$ in step S4, the light quantity of the second light source 51 is increased and the light quantity of the second light source 51 at a time $t_{b1}$ is stabilized. In the embodiment, after the time $t_{b1}$ in which the light quantity of the second light source 51 is stabilized, the pattern projection image can be acquired.

As shown in FIG. 2, the stripe pattern projected on the specimen becomes a pattern in which bright sections R1 by the white light source and dark sections R2 shaded by the stripe pattern generating unit 55 are alternately arranged.

Accordingly, this becomes a state in which an appropriate stripe is projected on the specimen from one place (hereinafter, this state is referred to as a "pattern projection state").

In addition, in the embodiment, while the time wa and the time wb shown in FIG. 4 are described as times until arriving at a stable state in which a light quantity of the illumination light or the projection light becomes constant, the time wa and the time wb may be times until arriving at the light quantity needed to acquire the image while the light quantity has yet to arrive at the stable state.

Figure 6:
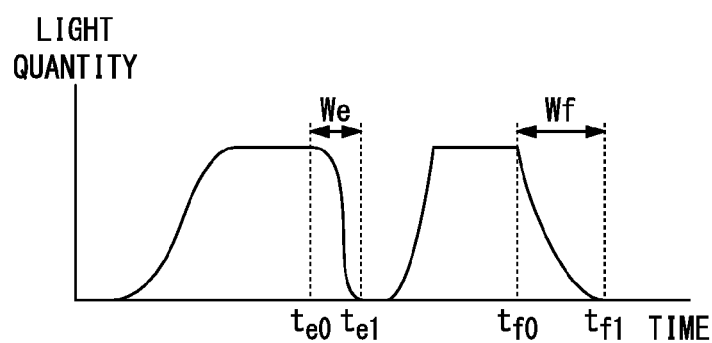
FIG. 6 is a graph showing a relation between a light quantity and time in use of an endoscope of a variant of the embodiment of the present invention.

Further, as shown in FIG. 6, a time we from stoppage of the first light source 41 that emits illumination light or starting of blocking of the illumination light until the light quantity of the illumination light is reduced to a light quantity that does not exert an influence on image acquisition, and a time wf from stoppage of the second light source 51 that emits the projection light or starting of the blocking of the projection light until the light quantity of the projection light is reduced to a light quantity does not exert an influence on image acquisition may be previously stored in the main control unit 22. In this case, the main control unit 22 is operated based on the above-mentioned time we and time wf. The main control unit 22 first operates one of the illumination unit 40 and the pattern projection unit 50, which has a short time until the light quantity is reduced to the light quantity having no influence to acquire the image. In addition, the main control unit 22 operates the other of the illumination unit 40 and the pattern projection unit 50 after that, which has a long time until the light quantity is reduced to the light quantity having no influence to acquire the image.

Furthermore, while not shown, when a total time D3, which is to be described below, is shorter than a total time D4, the main control unit 22 may first operate the illumination unit 40 and then operate the pattern projection unit 50. The total time D3 is a time in which a time from stoppage of the first light source 41 that emits illumination light or starting of blocking of the illumination light until the light quantity of the illumination light is reduced to a light quantity that does not exert an influence on acquiring the image and a time from starting of emission of the illumination light from the second light source 51 to arrival at the light quantity at which the light quantity of the illumination light is needed to acquire the image are added. In addition, the total time D4 is a time in which a time from stoppage of the second light source 51 that emits projection light or starting of blocking of the projection light until the light quantity of the projection light is reduced to a light quantity that does not exert an influence on acquiring the image and a time from starting of emission of the illumination light from the first light source 41 to arrival at the light quantity at which the light quantity of the illumination light is needed to acquire the image are added.

In addition, when the total time D4 is shorter than the total time D3, the main control unit 22 first operates the pattern projection unit 50 and then operates the illumination unit 40.

Further, in the embodiment, FIG. 4 or 6 shows an example in which the first light source 41 is completely turned off and then the second light source 51 is turned on. According to necessity, as the stoppage or blocking of the first light source 41 is started, turning on of the second light source 51 is immediately started, and a period in which the light quantity of the first light source 41 is reduced may overlap a period in which the light quantity of the second light source 51 is increased.

Accordingly, a time from the time $t_{a1}$ at which acquisition of a first image is started until acquisition of a second image is terminated in step S5 (to be described below) may be further reduced.

Here, step S4 is terminated and step S5 is performed.

Step S5 is a step of photographing a pattern projection image in the pattern projection state.

In step S5, the stripe pattern projected on the specimen becomes a pattern varied according to the 3-dimensional shape of the specimen. In this state, one image is acquired by the imager 31 of the image capturing unit 30 (hereinafter, an image photographed in the pattern projection state is referred to as a "pattern projection image").

The pattern projection image photographed in step S5 is temporarily stored on the RAM 24.

Here, step S5 is terminated and step S6 is performed.

In the embodiment, a time length D1 from the time $t_{a1}$ at which acquisition of the bright field image is started in step S3 to the time $t_{b2}$ at which acquisition of the pattern projection image is terminated in step S5 includes the time wb from starting of turning on of the second light source 51 until the light quantity of the second light source 51 is stabilized.

The time wb is shorter than the time wa from starting of turning on of the first light source 41 until the light quantity of the first light source 41 is stabilized. For this reason, in the case of the embodiment, as the second light source 51 is turned on after the first light source 41, an interval in which the two images (the bright field image and the pattern projection image) are acquired becomes shorter than that of the case in which the first light source 41 is turned on after the second light source 51.

In this way, in step S2 to step S5, the bright field image of the specimen is acquired using the illumination light having a longer time until the light quantity is stabilized, based on the time wa from starting of emission of the illumination light until the light quantity of the illumination light is stabilized and the time wb from starting of emission of the projection light until the light quantity of the projection light is stabilized. After the bright field image is acquired, in step S2 to step S5, the pattern projection image of the specimen is acquired using the projection light having a short time until the light quantity is stabilized.

Step S6 is a step of detecting a blur between the insertion unit 10 and the test object from step S2 to step S5 based on the images (the bright field image and the pattern projection image) photographed from step S2 to step S5.

In step S6, first, the same feature point is detected from the bright field image and the pattern projection image stored on the RAM 24, and coordinates of the feature point in the two images are calculated.

Here, step S6 is terminated and step S7 is performed.

Step S7 is a step of determining a blur of the two images using the feature point detected in step S6 and diverging the processing.

In step S7, when the coordinates of the feature point in the two images are the same coordinates in each of the images, it is determined that the blur is not generated from the initial image and the after-image, and step S8 is performed. On the other hand, when the coordinates of the feature point in the two images are different coordinates in the images, it is determined that a blur is generated from the initial image and the after-image, a message showing that photographing is necessary again since the blur is generated is displayed on the monitor 28 (step S11), and a series of processing is terminated.

Here, step S7 is terminated.

Step S8 is a step of allowing a user to select whether 3-dimensional measurement using the photographed pattern projection image is performed now or later.

In step S8, for example, inquiries such as "Perform measurement?" and so on are displayed on the monitor 28, and an input of determining whether the 3-dimensional measurement using the photographed pattern projection image is performed or not is prompted to the user.

When the input of determining that the measurement is performed is provided, step S9 is performed.

When the input of determining that the measurement is not performed is provided, step S12 is performed.

Here, step S8 is terminated.

Step S9 is a step of performing analysis for 3-dimensional measurement.

In step S9, analysis for a 3-dimensional shape is performed based on the pattern projection image stored on the RAM 24. For example, in the embodiment, the 3-dimensional shape of the specimen is analyzed by, for example, a known spatial phase shift method or Fourier transform method using one pattern projection image.

The analysis result of the 3-dimensional shape is generated as a text file or a binary file, and saved in the auxiliary storage device 25 with the pattern projection image. In addition, step S9 may be performed as background processing of step S8 simultaneously with starting of step S8.

Here, step S9 is terminated and step S10 is performed.

Step S10 is a step of transferring a display on the monitor 28 to the screen of various measuring modes and displaying a measurement result on the monitor 28 using information stored in step S10.

In step S10, the 3-dimensional shape of the specimen displayed on the bright field image is displayed on the monitor 28, while overlay-displaying a result analyzed in step S9 on the bright field image acquired in step S3, and so on. Accordingly, the user can perceive the 3-dimensional shape of the specimen.

Here, step S10 is terminated and a series of processing is terminated.

Step S12 is a step diverged from step S8, and a step of performing information processing needed for performing display of the measurement result after that.

In step S12, like step S9, based on the pattern projection image stored on the RAM 24, analysis of the 3-dimensional shape is performed. For example, in the embodiment, the 3-dimensional shape of the specimen is analyzed by, for example, a known spatial phase shift method or Fourier transform method using one pattern projection image.

In addition, the bright field image, the pattern projection image, the analysis result of the 3-dimensional shape, and optical parameters used for analysis are saved in the auxiliary storage device 25 as binary files or text files. In this case, for example, as portions of file names are shared in common or these files are saved in one directory (folder) at a time, these files are saved in the auxiliary storage device 25 to be read in a lump after that.

Here, step S12 is terminated and a series of processing is terminated.

As described above, according to the endoscope 1 and the image acquisition method of the embodiment, based on the time wa and the time wb until the light quantities of the first light source 41 and the second light source 51 are stabilized, acquisition of the bright field image using the first light source 41 having a long time until the light quantity is stabilized is performed first, and after the bright field image is acquired, the pattern projection image is acquired. For this reason, the interval of acquiring the bright field image and the pattern projection image can be reduced. Accordingly, a positional deviation between the plurality of acquired images can be suppressed.

In addition, even when a plurality of kinds of light sources having different times until the light quantity is stabilized are combined and used to optimize optical characteristics such as the light quantity, color, or the like, as the image is acquired at a sequence at which the positional deviation between the plurality of acquired images becomes minimal, it is possible for the result of analyzing the 3-dimensional shape using the pattern projection image to accurately correspond to a picture on the bright field image.

Further, the time from starting of acquisition of the image of the specimen to termination of acquisition of the image of the specimen can be reduced.

(Variant)

Next, variants of the endoscope 1 and the image acquisition method described in the above-mentioned embodiment will be described.

Figure 5:
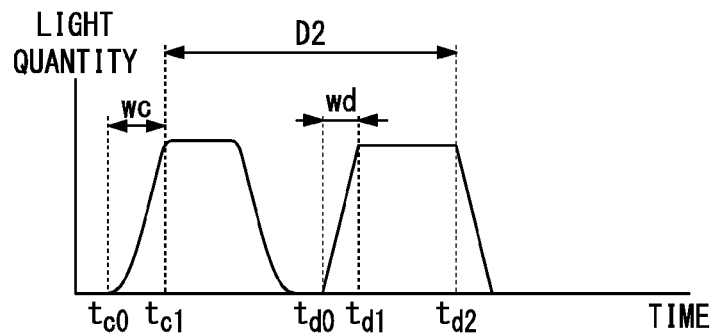
FIG. 5 is a graph showing a relation between a light quantity and time in use of an endoscope of a variant of the embodiment of the present invention.

FIG. 5 is a graph showing a relation between a light quantity and a time in use of an endoscope 1A of the variant.

The endoscope 1A (see FIG. 1) of the variant is distinguished from the above-mentioned endoscope 1 in that a first light source 41A having a shutter module is installed instead of the first light source 41. In addition, in the endoscope 1A of the variant, an operation of the main control unit 22 is different from that of the above-mentioned endoscope 1.

The shutter module of the first light source 41A is a shutter, an opening/closing operation of which is controlled by the light source control unit 21.

In the variant, the first light source 41A is turned on while the endoscope 1A is on. In the first light source 41A, as the shutter module is opened and closed, ON and OFF of the illumination light and the emission light quantity are adjusted according to control from the light source control unit 21. In addition, the light source control unit 21 configured to control the first light source 41A may have a power-saving circuit configured to turn off the first light source 41A when there is no need to image the bright field image.

In the variant, a time wd (see FIG. 5) from starting of emission of the illumination light from the first light source 41A having the shutter module until the light quantity of the illumination light is stabilized is a time from an opening operation of the shutter of the first light source 41A to complete opening of the shutter. The time wd is shorter than a time we (in the variant, having the same length as the time wb shown in FIG. 4) from starting of emission of the projection light from the second light source 51 until the light quantity of the projection light is stabilized.

According to the relation of the above-mentioned time we and time wd, in the illumination unit 40 and the pattern projection unit 50, the main control unit 22 first operates the pattern projection unit 50 having a long time until the light quantity is stabilized. In addition, in the illumination unit 40 and the pattern projection unit 50, the main control unit 22 later operates the illumination unit 40 having a short time until the light quantity is stabilized. Further, the main control unit 22 first acquires the stripe image with respect to the image capturing unit 30, and then acquires the bright field image after the pattern projection image is acquired.

In the endoscope 1A and the image acquisition method of the variant, as shown in FIG. 5, a time length D2 from a time $t_{c1}$ at which acquisition of the pattern projection image is started to a time $t_{d2}$ at which acquisition of the bright field image is terminated includes a time wd from an opening operation of the shutter of the first light source 41A to the complete opening of the shutter.

The time wd is shorter than a time we from starting of turning on of the second light source 51 until the light quantity of the second light source 52 is stabilized. For this reason, in the case of the variant, as the first light source 41A is turned on after the second light source 51, an interval of acquiring the two images (the bright field image and the pattern projection image) is smaller than the case in which the second light source 51 is turned on after the first light source 41A.

In this way, even in the endoscope 1A and image acquisition method of the variant, the same effect as the endoscope 1 and the image acquisition method described in the above-mentioned embodiment is exhibited.

In addition, since the first light source 41A having the shutter module is employed, the time wd from starting of emission of the light from the first light source 41A to stabilization of the light quantity of the first light source 41A depends on the time in which the shutter is opened and closed, rather than the time until the light quantity of the light source is stabilized. For this reason, the light source having a time applied until the light quantity is stabilized, and a selection degree of freedom of the light source is increased.

Hereinabove, while the embodiment of the present invention has been described with reference to the accompanying drawings, a specific constitution is not limited to the embodiment but design changes may be made without departing from the spirit of the present invention.

For example, in the above-mentioned embodiment, while an example in which a combination of the first light source and the second light source is constituted by a halogen lamp and an LED light source has been described, a combination in which the first light source is the LED light source and the second light source is the halogen lamp may be employed. In this case, since the second light source has a long time until the light quantity is stabilized, like the sequence shown in the above-mentioned variant, the main control unit is configured such that the pattern projection image is acquired first and the bright field image is acquired after that.

In addition, when the relation of the time until the light quantity is stabilized is not inverted even when the shutter module is installed at the light source, there is no need to change an acquisition sequence of the images.

Further, the shutter module may be installed at the second light source. Further, the shutter modules may be installed at both of the first light source and the second light source.

Furthermore, in the above-mentioned embodiment and variant, while the endoscope configured such that the stripe pattern is projected from one place of the tip surface of the insertion unit has been described, the endoscope may be configured such that stripe patterns having different phases are projected from a plurality of places of the tip surface of the insertion unit. Even in this case, the same effects as described in the above-mentioned embodiment and variant is exhibited.

In addition, a plurality of illumination windows may be opened at the tip surface of the insertion unit.

Further, in the above-mentioned embodiment, while an example in which only one pattern projection image is acquired has been described, analysis of the 3-dimensional shape may be performed by a time phase shift method of projecting a plurality of stripe patterns having different phases on the specimen and acquiring a plurality of pattern projection images having different phases.

Furthermore, in the above-mentioned embodiment, after the pattern projection image is acquired, the bright field image may be acquired again. In this case, a blur can be detected using the bright field image acquired before and after the pattern projection image is acquired.

In addition, pluralities of pattern projection images and bright field images may be acquired, and an optimal image may be appropriately selected to analyze the 3-dimensional shape and detect the blur.

Further, the light quantity needed to acquire the bright field image and the light quantity needed to acquire the pattern projection image may be different from each other. In this case, the light quantity emitted from the first light source and the light quantity emitted from the second light source may be different from each other.

In addition, components shown in the above-mentioned embodiment and variant may be appropriately combined and configured.

According to the endoscope and the image acquisition method, the positional deviation between the acquired images can be suppressed.

While preferred embodiments of the present invention have been described and illustrated above, it should be understood that these are examples of the present invention and are not to be considered as limiting. Additions, omissions, substitutions, and other modifications can be made without departing from the scope of the present invention. Accordingly, the present invention is not to be considered as being limited by the foregoing description, and is only limited by the scope of the claims.

What is claimed is:

1. An endoscope configured to measure a specimen using a pattern projection image of the specimen on which a light and shade pattern of light is projected, the endoscope comprising:
    an insertion unit;
    an image capturing unit installed at a tip section of the insertion unit and configured to acquire an image of the specimen;
    an illumination unit having a first light source configured to emit illumination light to illuminate an observation field of vision of the image capturing unit;
    a pattern projection unit having a second light source configured to emit projection light to project the light and shade pattern on the specimen; and
    a control unit configured to control an operation of acquiring the image by the image capturing unit, a first power of the illumination light from the illumination unit, and a second power of the projection light from the pattern projection unit,
    wherein, in the control unit,
    based on a first time from starting the first power of the illumination light from the first light source until light quantity of the illumination light arrives at a light quantity needed to acquire the image, and a second time from starting the second power of the projection light from the second light source until light quantity of the projection light arrives at a light quantity needed to acquire the image,
    one of the illumination unit and the pattern projection unit, which has a longer time until the light quantity arrives at the light quantity needed to acquire the image, is operated first so that a first image of the specimen is acquired by the image capturing unit, and
    the other of the illumination unit and the pattern projection unit, which has a shorter time until the light quantity arrives at the light quantity needed to acquire the image, is started after acquisition of the first image so that a second image of the specimen is acquired by the image capturing unit.

2. The endoscope according to claim 1, wherein, in the control unit,
- based on a time from starting of supply stoppage of the illumination light until the light quantity of the illumination light is reduced to a light quantity that does not exert an influence on acquisition of the image, and a time from starting of supply stoppage of the projection light until the light quantity of the projection light is reduced to a light quantity that does not exert an influence on acquisition of the image,
- one of the illumination unit and the pattern projection unit, which has a shorter time until the light quantity is reduced to a light quantity that does not exert an influence on acquisition of the image, is operated first so that the first image of the specimen is acquired by the image capturing unit, and
- the other of the illumination unit and the pattern projection unit, which has a longer time until the light quantity is reduced to a light quantity that does not exert an influence on acquisition of the image, is operated after acquisition of the first image so that the second image of the specimen is acquired by the image capturing unit.

3. The endoscope according to claim 2, wherein the supply stoppage of the illumination light comprises stoppage of the first light source that emits the illumination light.

4. The endoscope according to claim 2, wherein the supply stoppage of the illumination light comprises blocking of the illumination light.

5. The endoscope according to claim 2, wherein the supply stoppage of the projection light comprises stoppage of the second light source that emits the projection light.

6. The endoscope according to claim 2, wherein the supply stoppage of the projection light comprises blocking of the projection light.

7. The endoscope according to claim 1, wherein, in the control unit,
- when (i) a total time of a time from starting of supply stoppage of the illumination light until the light quantity of the illumination light is reduced to a light quantity that does not exert an influence on acquisition of the image, and a time from starting of emission of the illumination light from the second light source until the light quantity of the illumination light arrives at a light quantity needed to acquire the image, is smaller than (ii) a total time of a time from starting of supply stoppage of the projection light until the light quantity of the projection light is reduced to a light quantity that does not exert an influence on acquisition of the image, and a time from starting of emission of the illumination light from the first light source until the light quantity of the illumination light arrives at a light quantity needed to acquire the image,
- the illumination unit is operated first so that the first image of the specimen is acquired by the image capturing unit, and then the pattern projection unit is operated so that the second image of the specimen is acquired by the image capturing unit.

8. The endoscope according to claim 1, wherein, in the control unit,
- when (i) a total time of a time from starting of supply stoppage of the illumination light until the light quantity of the illumination light is reduced to a light quantity that does not exert an influence on acquisition of the image, and a time from starting of emission of the illumination light from the second light source until the light quantity of the illumination light arrives at a light quantity needed to acquire the image, is larger than (ii) a total time of a time from starting supply stoppage of the projection light until the light quantity of the projection light is reduced to a light quantity that does not exert influence on acquisition of the image, and a time from emission of the illumination light from the first light source until the light quantity of the illumination light arrives at a light quantity needed to acquire the image,
- the pattern projection unit is operated first so that the first image of the specimen is acquired by the image capturing unit, and then the illumination unit is operated so that the second image of the specimen is acquired by the image capturing unit.

9. The endoscope according to claim 1, wherein a shutter configured to switch an emission state of light is installed at at least one of the first light source and the second light source.

10. The endoscope according to claim 1, wherein the control unit comprises a blur detection unit configured to select at least two images from among an image of the specimen acquired in a state in which the illumination light is radiated and an image of the specimen acquired in a state in which the projection light is radiated, and to detect a blur of the insertion unit and the specimen based on a deviation amount of the at least two images.

\* \* \* \* \*